United States Patent [19]

Schwerdtel et al.

[11] Patent Number: 4,548,913

[45] Date of Patent: Oct. 22, 1985

[54] CATALYST, A PROCESS FOR ITS PREPARATION AND AN ISOMERIZATION PROCESS IN THE PRESENCE OF THIS CATALYST

[75] Inventors: Wulf Schwerdtel, Leverkusen; Hubert Lauer, Dormagen; Josef Heinrich, Langenfeld, all of Fed. Rep. of Germany

[73] Assignee: Bayer Aktiengesellschaft, Leverkusen, Fed. Rep. of Germany

[21] Appl. No.: 560,356

[22] Filed: Dec. 12, 1983

[30] Foreign Application Priority Data

Dec. 16, 1982 [DE] Fed. Rep. of Germany ....... 3246495

[51] Int. Cl.4 .......................... B01J 29/28; B01J 21/16
[52] U.S. Cl. ......................................... 502/68; 502/71
[58] Field of Search ............................. 502/68, 71, 77

[56] References Cited

U.S. PATENT DOCUMENTS

| 2,973,327 | 2/1961 | Mitchell et al. | 502/68 X |
| 3,384,602 | 5/1968 | Robinson | 252/455 Z |
| 3,641,095 | 2/1972 | Kiovsky et al. | 502/68 |
| 3,660,513 | 5/1972 | Davison | 260/680 E |
| 3,997,474 | 12/1976 | Miale et al. | 252/450 |
| 4,101,598 | 7/1978 | Whittam et al. | 260/688 A |
| 4,211,886 | 7/1980 | Tabak et al. | 585/321 |
| 4,247,416 | 1/1981 | Doherty et al. | 502/68 X |
| 4,324,698 | 4/1982 | Lewis et al. | 252/455 Z |

FOREIGN PATENT DOCUMENTS 0035807 9/1981 European Pat. Off. .
0051318 5/1982 European Pat. Off. .

Primary Examiner—Carl F. Dees
Attorney, Agent, or Firm—Sprung Horn Kramer & Woods

[57] ABSTRACT

A new catalyst which can be prepared from certain aluminosilicates and certain clay minerals, a process for its preparation and a process for the skeletal isomerization of n-alkenes to iso-alkenes which is carried out in the presence of this catalyst.

2 Claims, No Drawings

CATALYST, A PROCESS FOR ITS PREPARATION AND AN ISOMERIZATION PROCESS IN THE PRESENCE OF THIS CATALYST

The present invention relates to a new catalyst which can be prepared from certain aluminosilicates and certain clay minerals, a process for its preparation and a process for the skeletal isomerization of n-alkenes to iso-alkenes which is carried out in the presence of this catalyst.

The demand for iso-alkenes, in particular those having 4 to 5 C atoms, has recently been increasing steadily. For example, relatively large amounts of isobutene are required for the production of methyl tert.-butyl ether, the importance of which as a lead-free fuel improver is increasing constantly.

Processes for the catalytic skeletal isomerization of n-alkenes to iso-alkenes are known, but these processes all have disadvantages because the catalysts known hitherto have a short time-on-stream and have to be regenerated frequently. Examples of known catalysts are activated aluminum oxides, such as eta- or gamma-$Al_2O_3$, halogenated aluminum oxides, bauxite, aluminum oxides treated with compounds of boron, zirconium or silicon, phosphates and solid phosphoric acids.

Thus, British Patent No. 2,060,424 describes an isomerization catalyst for converting linear aliphatic olefins to branched aliphatic olefines, which catalyst contains active aluminum oxide and, deposited thereon, fluorine and chlorine. According to the examples, the reaction time over this catalyst is 1 or 2 hours. German Patent A No. 3,118,199 describes a skeletal isomerization in which a fluorinated aluminum oxide is employed as the catalyst, and the reaction is carried out in the presence of particular amounts of steam. Regarding these catalysts, German Patent A No. 3,000,650 states that, as a result of the addition of steam, fluorine is removed from the catalyst and the catalyst is very rapidly deactivated. In order to maintain the catalyst activity, it is proposed to meter in fluorine compounds subsequently. As a result, the time between two catalyst regenerations can be increased to approx. 50 hours, but this is still very unsatisfactory. German Patent A No. 2,534,459 describes a process for the isomerization of alkenes, in which a catalyst is employed with is prepared by treating active aluminum oxide with certain low molecular weight silicon compounds. This catalyst has to be regenerated after only 15 to 20 hours.

European Patent A No. 35,807 describes catalytic reactions over catalysts consisting of so-called silicalite. Silicalite is a member of the pentasil family (for a definition of the pentasil family, see W. M. Meyer and G. T. Kokotailo, "The Properties and Applicationsof Zeolites", page 133, The Chemical Society, London 1979), of which a large number are known, for example the ZSM types, especially ZSM-5 and the Nu types, and a certain crystalline silicon dioxide which can contain small amounts of aluminum oxide (see German Patent A No. 2,751,443). According to the data in European Patent A No. 35,807, the silicalite is obtained in the form of a fine powder in its preparation. If it is to be used as a catalyst in lumps, it can be mixed with a binder, for example kaolin, and the mixture can be moulded. However, kaolin can only act as a binder if the mixture of silicalite and kaolin is heated to temperatures above 550° C., since kaolin is converted to metakaolin only at above 550° C. (see Ullmann, Enzyklopädie der technischen Chemie [Encyclopaedia of Industrial Chemistry], 4th edition, Volume 17, page 587).

European Patent No. 35,807 does not indicate that advantageous catalysts can be obtained from mixtures of crystalline alumino silicates and kaolinite-containing clay minerals, which are calcined at a maximum of 550° C., that is to say substantially below the binding temperature of kaolin.

A catalyst has now been found which is characterized in that it is obtainable by a process in which a crystalline aluminosilicate which has a molar ratio of silicon to aluminum of 100:1 to 10,000:1 is mixed with a kaolinite-containing clay mineral, binders, and/or fillers are, if required, added to the mixture, the latter is moulded and the mouldings are calcined at 350° to 550° C.

Preferably used crystalline aluminosilicates are aluminosilicates of the zeolite type, in particular those having the structural features of the pentasil family. Crystalline aluminosilicates as described in U.S. Pat. Nos. 3,702,886, 4,061,724, 3,748,251, British No. 1,117,568 (ZSM-4), U.S. Pat. Nos. 3,709,979 (ZSM-11), 3,832,449 (ZSM-12) and German Patent A No. 2,751,443 are particularly preferred.

The crystalline aluminosilicate preferably has a molar ratio of silicon to aluminum of 300:1 to 5,000:1.

Particularly suitable kaolinite-containing clay minerals are kaolin and clay minerals which contain kaolin. For example, clay minerals which contain 20 to 100% by weight of kaolin are suitable.

Mixing of the crystalline aluminosilicate and the kaolinite-containing clay mineral can be carried out in a customary manner. If these starting materials are not already in a finely pulverulent form, they are advantageously finely milled, if desired, with the addition of auxiliaries, for example water.

It it is desired to obtain the catalysts according to the invention in pulverulent form, the mixture of the crystalline aluminosilicate and the kaolinite-containing clay mineral can be calcined at 350° to 550° C., without further pretreatment. It it is desired to obtain catalysts in the form of lumps, the mixture of the crystalline aluminosilicate and kaolinite-containing clay mineral can be mixed with customary binders and/or customary fillers, and first the mixture can be moulded and thereafter the mouldings can be calcined at 350° to 550° C., preferably at 450° to 550° C. In general, times in the range from 1 to 5 hours are sufficient for the calcination. The weight ratio of crystalline aluminosilicate to kaolinite-containing clay material can be, for example, in the range from 0.4:1 to 20:1. This weight ratio is preferably 1.5:1 to 9:1.

A preferred embodiment of the catalyst according to the invention is obtainable if a crystalline alumino-silicate is employed which contains 0.05 to 2% by weight of fluorine. The procedure can be carried out as follows: the crystalline aluminosilicate is treated, before being mixed with kaolinite-containing clay mineral, with a fluorine compound until the fluorine content is 0.05 to 2% by weight. Examples of suitable fluorine compounds are hydrogen fluoride, ammonium fluoride, fluoboric acid, fluorisilicic acid and organic fluorine compounds. The treatment can, for example, be carried out as follows: the crystalline aluminosilicate is impregnated with a solution of a fluorine compound, for example with an aqueous ammonium fluoride solution, and thereafter the crystalline aluminosilicate impregnated in this manner is dried, and calcined at 450°–550° C.

A further preferred embodiment of the catalyst according to the invention is obtainable if a kalolinite-containing clay material which has been pretreated with a solution of one or more alkali metal and/or alkaline earth metal salts is employed. This pretreatment can, for example, be carried out as follows: the kaolinite-containing clay mineral is impregnated with an excess of an aqueous solution of a water-soluble alkali metal salt and/or a water-soluble alkaline earth metal salt, for example at an elevated temperature, and the kaolinite-containing clay mineral is then washed thoroughly with water and dried.

A particularly preferred embodiment is a combination of a fluorine-containing crystalline aluminosilicate and a kaolinite-containing clay mineral pretreated with alkali metal and/or alkaline earth metal salts.

The present invention furthermore relates to a process for the preparation of a catalyst, which is characterised in that a crystalline aluminosilicate which has a molar ratio of silicon to aluminum of 100:1 to 10,000:1 is mixed with a kaolinite-containing clay mineral, binders and/or filters are, if required, added to the mixture, the latter is moulded and the mouldings are calcined at 350° to 550° C. In the preparation of the catalyst, the preferred measures are those which have been described above for the catalyst as such. Preferably, a crystalline aluminosilicate which contains 0.05 to 2% by weight of fluorine, and a kaolinite-containing clay mineral which has been pretreated with a solution of one or more alkali metal and/or alkaline earth metal salts, are employed.

Mixing of the aluminosilicate and the kaolinite-containing clay mineral can be carried out in any desired manner, for example, by mixing the dry materials or the pulverulent materials, for example moistened with water. If the starting materials are calcined as pulverulent substances without the addition of binders and/or fillers, the catalysts according to the invention are obtained in powder form. For use in fluidized-bed reactors, the catalysts according to the invention can be prepared, for example, as microgranules, for example by spray-granulation techniques which are in themselves known. It is also possible to prepare catalysts according to the invention in the form of lumps, which form is suitable for use as fixed-bed catalysts. For this purpose, it is necessary to add binders and/or fillers to the mixture of the crystalline aluminosilicate and the kaolinite-containing clay mineral, and then to mould the mixture. Examples of suitable binders are silica sol or silica gel, and suitable fillers are preferably inert, such as amorphous silicon dioxide. Moulding can be effected by known methods, for example by extruding, pelletizing or compressing. If binders and/or fillers are employed in the catalyst preparation, and moulding is carried out, it is advantageous if the properties obtained after this treatment are first dried and then calcined at temperatures of 350° to 550° C.

The present invention furthermore relates to a process for the catalytic skeletal isomerization of n-alkenes to iso-alkenes, which is characterized in that the isomerization is carried out in the presence of catalysts which are obtainable by a process in which a crystalline aluminosilicate which has a molar ratio of silicon to aluminium of 100:1 to 10,000:1 is mixed with a kaolinite-containing clay mineral, binders and/or fillers are, if required added to the mixture, the latter is moulded and the mouldings are calcined at 350° to 550° C.

In the process, according to the invention, for the catalytic skeletal isomerization, or where the catalysts according to the invention are used in the skeletal isomerization, the preferred measures with respect to the catalyst are those which have been described above for the catalyst as such and for its preparation.

The catalytic skeletal isomerization according to the invention is carried out in general in the gas phase at reaction temperatures in the range from 350° to 550° C., preferably in the range from 450° to 550° C. Moreover, the catalyst can be in the form of a fixed bed in a reactor, but it is also possible to carry out the reaction in a moving bed, for example in a fluidized bed.

To carry out the isomerization in a fluidized bed, suitable catalysts are pulverulent catalysts or those in the form of microgranules; that is to say, in the preparation of such catalysts, it is, as described above, not necessary to add binders and/or fillers to the mixture of the crystalline aluminosilicate and the kaolinite-containing clay mineral and to mould the mixture.

To carry out the isomerization using fixed-bed catalysts, suitable catalysts are those which are in the form of lumps and can be prepared as described above.

Using the process according to the invention, it is possible to isomerize any desired n-alkenes to iso-alkenes, for example those having 3 to 10 C atoms. Preferably, n-alkenes having 4 to 6 carbon atoms, particularly preferably n-alkenes having 4 carbon atoms (n-butenes) and those having 5 carbon atoms (n-pentenes), are subjected to the skeletal isomerization process according to the invention. The n-alkenes can be employed in pure form, as mixtures with one another or as mixtures with other hydrocarbons, in particular with the corresponding alkanes. It may be advantageous to dilute the n-alkenes, or the starting mixtures containing n-alkenes, with gases. Examples of suitable substances for this purpose are: nitrogen, carbon dioxide and/or steam. Steam, in particular, is advantageous in the reaction in that the catalyst activity, together with high selectivity, is maintained over very long operating periods. The amount of steam added can vary within wide limits, but a molar ratio of water to hydrocarbons employed of 0.01:1 to 10:1 is particularly advantageous.

Suitable operating pressures for the skeletal isomerization according to the invention are, for example, pressures from 0.1 to 10 bar. Pressures in the range from 1 to 5 bar are preferred.

In the skeletal isomerization according to the invention, the weight hourly space velocity, expressed as WHSV, can be, for example, in the range from 0.1 to 20. The weight hourly space velocity is preferably from 0.2 to 10 kg of n-alkenes per liter of catalyst per hour.

The residence time of the starting materials in the reaction zone is preferably less than 5 seconds in the process according to the invention.

If, in the catalytic skeletal isomerization according to the invention, the activity of the catalysts diminishes after a relatively long operating time, they can be readily regenerated by known methods. For example, air or air/steam mixtures can be passed over the catalyst at temperatures of, for example, 400° to 550° C.

When they are employed in the catalytic skeletal isomerization of n-alkenes to iso-alkenes, the catalysts according to the invention have the advantage that, in comparison to known catalysts, they permit very much longer operating times before they have to be regenerated. The operating time of the catalysts according to the invention is in general several hundred hours and can be up to more than 1,000 hours.

Catalysts according to the invention which have been prepared using a fluorine-containing crystalline aluminosilicate are particularly active. Catalysts according to the invention which have been prepared using a kaolinite-containing clay mineral treated with alkali metal and/or alkaline earth metal salts exhibit particularly good selectivities for the conversion of n-alkenes to iso-alkenes.

In contrast to European Patent A No. 35,807, in the present invention the kaolinite-containing clay mineral does not act as a binder but constitutes an essential part of the catalyst. The catalyst according to the invention is effective in the skeletal isomerization only if the aluminosilicate and the kaolinite-containing clay mineral are present together. The individual components do not exhibit catalytic activity in the skeletal isomerization. Substances which are likewise catalytically inactive in the skeletal isomerization are obtained if the aluminosilicate and the kaolinite-containing clay minerals are calcined at temperatures at which conversion of the kaolinite to metakaolin takes place (see Example 6).

The examples which follow illustrate the invention without restricting it in any way.

EXAMPLES

Definitions of terms used in the examples below:

C$_4$ starting material:
A hydrocarbon mixture having the composition
| | |
|---|---|
| isobutane | 6.90% by weight |
| n-butane | 22.80% by weight |
| n-but-1-ene | 37.80% by weight |
| i-butene | 0.90% by weight |
| t-but-2-ene | 11.20% by weight |
| i-but-2-ene | 20.40% by weight |

WHSV: weight hourly space velocity = kg of starting material per liter of catalyst per hour.
C$_{5+}$: Products having 5 or more carbon atoms.
$\leq$C$_3$: Products having 1 to 3 carbon atoms.
Conversion of n-butenes (%):
$$\frac{(\Sigma\ \%\ \text{n-butenes}_{initial} - \Sigma\ \%\ \text{n-butenes}_{final}) \cdot 100}{\Sigma\ \text{n-butenes}_{initial}}$$

Selectivity for isobutene (%):
$$\frac{(\%\ \text{isobutene}_{initial} - \%\ \text{isobutene}_{final}) \cdot 100}{\Sigma\ \%\ \text{n-butenes}_{initial} - \Sigma\ \%\ \text{n-butenes}_{final}}$$

Selectivity for propene (%):
$$\frac{\%\ \text{propene} \cdot 100}{\Sigma\ \%\ \text{n-butenes}_{initial} - \Sigma\ \%\ \text{n-butenes}_{final}}$$

Selectivity for C$_{5+}$ (%):
$$\frac{\%\ C_{5+} \cdot 100}{\Sigma\ \%\ \text{n-butenes}_{initial} - \Sigma\ \%\ \text{n-butenes}_{final}}$$

Selectivity for $\leq$C$_3$ (%):
$$\frac{\%\ \leq C_3 \cdot 100}{\Sigma\ \%\ \text{n-butenes}_{initial} - \Sigma\ \%\ \text{n-butenes}_{final}}$$

Space/time yield for isobutene:
Space/time yield = g of isobutene per liter of catalyst per hour.

EXAMPLE 1

7 kg of water and 0.3 kg of concentrated sodium hydroxide solution were initially introduced into a stirred autoclave. 0.4 kg of tetrapropylammonium bromide was dissolved in this mixture, and the mixture was stirred for 15 minutes. Thereafter, 6 kg of silica sol (30% strength) were introduced into the stirred mixture sufficiently slowly for a homogeneous mixture to be formed. The resulting gel was crystallized in the course of 5 days at 150° C. The crystalline aluminosilicate thus obtained had the X-ray interplanar spacings typical of pentasils and contained silicon and aluminium in a molar ratio of 440:1.

50 g of this aluminosilicate together with 10 g of kaolin of the Dorfner H 1 type were suspended in 25 g of water, and the components were mixed. The mixture was pressed through a perforated plate and the product was dried. The product moulded in this manner was then calcined for 3 hours at 450° C.

The catalyst prepared in this manner was introduced into an electrically heated tube reactor having a volume of 30 ml. By means of a mechanical metering device, the C$_4$ starting mixture and steam were metered in. The reaction temperature was 500° C. The gas stream emerging from the reactor was investigated by means of gas chromatography. The results shown in Table 1 were obtained.

TABLE 1

| | Hours of operation | | | | | | | |
|---|---|---|---|---|---|---|---|---|
| | 12 | 24 | 36 | 48 | 60 | 72 | 84 | 96 |
| WHSV for C$_4$ starting material | 1.64 | 1.64 | 1.69 | 1.61 | 1.67 | 1.69 | 1.67 | 1.67 |
| WHSV for steam | 0.5 | 0.5 | 0.5 | 0.5 | 0.5 | 0.5 | 0.5 | 0.5 |
| Isobutene (% by weight) | 6.56 | 5.57 | 4.69 | 7.78 | 7.47 | 6.60 | 5.90 | 5.07 |
| Propene (% by weight) | 1.23 | 1.27 | 1.33 | 1.30 | 1.28 | 1.29 | 1.21 | 1.20 |
| n-Butane (% by weight) | 22.65 | 22.83 | 22.75 | 23.02 | 23.20 | 22.96 | 23.13 | 23.15 |
| n-But-1-ene (% by weight) | 16.91 | 16.99 | 17.28 | 16.48 | 16.63 | 16.79 | 17.03 | 17.04 |
| i-Butene (% by weight) | 8.42 | 8.16 | 8.21 | 8.10 | 7.81 | 7.55 | 7.69 | 7.87 |
| t-But-2-ene (% by weight) | 24.25 | 24.40 | 24.70 | 23.67 | 23.59 | 24.50 | 24.58 | 25.00 |
| i-But-2-ene (% by weight) | 17.50 | 18.01 | 18.25 | 17.17 | 17.41 | 17.64 | 17.79 | 17.98 |
| C$_{5+}$ (% by weight) | 2.43 | 2.71 | 2.73 | 2.44 | 2.54 | 2.81 | 2.41 | 2.63 |
| $\leq$C$_3$ (% by weight) | 0.05 | 0.05 | 0.06 | 0.04 | 0.06 | 0.05 | 0.06 | 0.06 |
| Conversion of n-butene (%) | 22.5 | 22.7 | 22.9 | 25.5 | 26.6 | 24.1 | 24.6 | 24.4 |
| Selectivity for isobutene (%) | 69.4 | 66.8 | 66.6 | 68.2 | 66.8 | 64.7 | 67.6 | 66.9 |
| Selectivity for propene (%) | 10.2 | 10.4 | 10.8 | 10.9 | 11.0 | 11.0 | 10.6 | 10.2 |
| Selectivity for C$_{5+}$ (%) | 20.2 | 22.2 | 22.1 | 20.5 | 21.7 | 24.0 | 21.2 | 22.4 |
| Space/time yield for isobutene | 138.0 | 133.8 | 138.7 | 130.4 | 130.4 | 127.6 | 128.4 | 131.4 |

EXAMPLE 2

50 g of the crystalline aluminosilicate prepared as described in Example 1 were suspended in a solution of 1 g of ammonium fluoride in 50 ml of water. After drying, and calcining for 3 hours at 450° C., the material contained 0.35% by weight of fluorine. This fluorine-containing crystalline aluminium silicate was mixed with kaolin so that the weight ratio of crystalline aluminium silicate to kaolin was 4:1. This mixture was mixed with water by a procedure similar to that described in Example 1, the mixture was converted to mouldings by pressing it through a perforated plate and drying the product, and the mouldings were then calcined for 3 hours at 450° C.

The catalyst prepared in this manner was employed, in accordance with the procedure described in Example 1, for the conversion of n-butene to iso-butene. The results obtained are summarized in Table 2.

EXAMPLE 3

50 g of the crystalline aluminosilicate prepared as described in Example 1 were fluorinated as described in Example 2. 20 g of kaolin were stirred with 300 ml of aqueous 2N $MgCl_2$ solution for 3 hours at 100° C. The kaolin treated in this manner was filtered off, washed with water and dried. Thereafter, 40 g of the fluorinated aluminosilicate and 6 g of the treated kaolin were mixed, the mixture was converted to mouldings by moulding through a perforated plate in a manner similar to that described in Example 1, and the mouldings were then calcined for 3 hours at 450° C.

The catalyst prepared in this manner was employed in accordance with the procedure described in Example 1 for the conversion of n-butene to iso-butene. The results obtained are summarized in Table 3.

TABLE 3

| | Hours of operation | | | | | | | |
|---|---|---|---|---|---|---|---|---|
| | 12 | 24 | 48 | 96 | 144 | 192 | 240 | 288 |
| WHSV for $C_4$ starting material | 2.94 | 2.83 | 3.0 | 3.05 | 3.05 | 3.05 | 2.94 | 2.17 |
| WHSV for steam | 2.33 | 2.33 | 2.33 | 2.09 | 2.05 | 2.03 | 2.0 | 2.0 |
| Isobutene (% by weight) | 4.09 | 7.45 | 6.50 | 8.30 | 2.91 | 4.00 | 6.19 | 7.13 |
| Propene (% by weight) | 2.98 | 3.17 | 3.22 | 2.91 | 2.98 | 2.85 | 2.61 | 2.37 |
| n-Butane (% by weight) | 23.43 | 23.69 | 23.76 | 23.76 | 23.05 | 23.58 | 24.24 | 23.70 |
| n-But-1-ene (% by weight) | 15.08 | 13.84 | 14.01 | 14.03 | 15.38 | 15.19 | 15.02 | 14.16 |
| i-Butene (% by weight) | 13.92 | 14.02 | 14.33 | 13.72 | 14.30 | 14.00 | 14.00 | 15.36 |
| t-But-2-ene (% by weight) | 19.87 | 18.53 | 18.76 | 18.36 | 20.43 | 20.01 | 18.29 | 18.88 |
| i-But-2-ene (% by weight) | 15.50 | 14.32 | 14.42 | 14.35 | 15.81 | 15.58 | 15.33 | 14.25 |
| $C_{5+}$ (% by weight) | 4.99 | 4.82 | 4.97 | 4.42 | 5.00 | 4.66 | 4.29 | 3.99 |
| $\leq C_3$ (% by weight) | 0.14 | 0.16 | 0.03 | 0.15 | 0.14 | 0.13 | 0.03 | 0.16 |
| Conversion of n-butene (%) | 32.5 | 34.4 | 35.4 | 40.2 | 33.2 | 33.2 | 34.8 | 38.2 |
| Selectivity for iso-butene (%) | 63.1 | 63.2 | 63.5 | 64.7 | 63.8 | 64.7 | 66.9 | 70.2 |
| Selectivity for propene (%) | 13.5 | 14.5 | 14.3 | 13.7 | 13.3 | 13.2 | 12.5 | 10.9 |
| Selectivity for $C_{5+}$ (%) | 22.7 | 21.7 | 22.0 | 20.8 | 22.3 | 21.5 | 20.5 | 18.2 |
| Selectivity for $\leq C_3$ (%) | 0.7 | 0.6 | 0.2 | 0.8 | 0.6 | 0.6 | 0.1 | 0.7 |
| Space/time yield for isobutene | 409.2 | 396.8 | 429.9 | 418.5 | 436.2 | 427.0 | 411.6 | 333.3 |

EXAMPLE 4

37.5 g of the aluminosilicate prepared as described in Example 1 and treated with ammonium fluoride as described in Example 2 were mixed with 12.5 g of kaolin treated with $MgCl_2$ solution as described in Example 3, the mixture was moulded by a procedure similar to that described in Example 1, and the mouldings were then calcined for 3 hours at 500° C.

The catalyst prepared in this manner was employed in accordance with the procedure described in Example

TABLE 2

| | Hours of operation | | | | | | |
|---|---|---|---|---|---|---|---|
| | 12 | 24 | 48 | 72 | 96 | 108 | 120 |
| WHSV for $C_4$ starting material | 1.67 | 1.72 | 1.53 | 1.75 | 1.61 | 1.64 | 1.58 |
| WHSV for steam | 0.5 | 0.5 | 0.5 | 0.5 | 0.5 | 0.5 | 0.5 |
| Isobutene (% by weight) | 6.10 | 5.10 | 8.11 | 6.76 | 5.06 | 3.89 | 7.73 |
| Propene (% by weight) | 5.99 | 5.18 | 3.44 | 3.51 | 3.49 | 3.69 | 3.30 |
| n-Butane (% by weight) | 20.67 | 20.77 | 20.16 | 20.22 | 20.62 | 20.13 | 22.21 |
| n-But-1-ene (% by weight) | 12.42 | 13.34 | 13.20 | 14.13 | 14.72 | 14.92 | 12.97 |
| i-Butene (% by weight) | 15.50 | 15.02 | 13.82 | 13.40 | 13.95 | 14.09 | 15.61 |
| t-But-2-ene (% by weight) | 18.03 | 19.14 | 19.26 | 20.94 | 21.31 | 21.60 | 19.23 |
| i-But-2-ene (% by weight) | 13.30 | 14.19 | 14.55 | 15.38 | 15.69 | 15.94 | 13.94 |
| $C_{5+}$ (% by weight) | 7.54 | 6.89 | 7.14 | 5.13 | 4.94 | 5.50 | 4.60 |
| $\leq C_3$ (% by weight) | 0.4 | 0.37 | 0.32 | 0.53 | 0.22 | 0.24 | 0.41 |
| Conversion of n-butene (%) | 43.6 | 41.4 | 41.5 | 36.4 | 36.3 | 32.0 | 34.6 |
| Selectivity for iso-butene (%) | 52.7 | 54.7 | 55.9 | 60.2 | 61.7 | 59.9 | 62.1 |
| Selectivity for propene (%) | 20.4 | 18.8 | 13.9 | 15.8 | 15.4 | 15.4 | 15.7 |
| Selectivity for $C_{5+}$ (%) | 25.6 | 25.1 | 28.9 | 23.0 | 21.8 | 23.4 | 21.3 |
| Selectivity for $\leq C_3$ (%) | 1.3 | 1.4 | 1.3 | 1.0 | 1.1 | 1.3 | 0.9 |
| Space/time yield for isobutene | 258.8 | 258.3 | 211.4 | 234.5 | 224.6 | 231.1 | 246.6 |

1 for the conversion of n-butene to isobutene. The results obtained are summarized in Table 4.

TABLE 4

| | Hours of operation | | | | | | | | | |
|---|---|---|---|---|---|---|---|---|---|---|
| | 100 | 200 | 300 | 400 | 500 | 600 | 700 | 800 | 900 | 1,000 |
| WHSV for $C_4$ starting material | 2.33 | 2.33 | 2.33 | 2.5 | 2.5 | 2.5 | 2.44 | 2.31 | 2.39 | 2.47 |
| WHSV for steam | 2.0 | 2.0 | 2.0 | 2.0 | 2.0 | 2.0 | 2.0 | 2.0 | 2.0 | 2.0 |
| Isobutene (% by weight) | 4.23 | 8.22 | 8.39 | 6.17 | 5.33 | 4.41 | 3.14 | 8.29 | 8.09 | 7.68 |
| Propene (% by weight) | 4.49 | 3.33 | 3.79 | 3.47 | 3.50 | 3.91 | 3.71 | 3.05 | 3.13 | 3.25 |
| n-Butane (% by weight) | 23.33 | 23.48 | 23.42 | 23.76 | 23.74 | 23.69 | 23.06 | 23.56 | 23.56 | 23.72 |
| n-But-1-ene (% by weight) | 13.06 | 12.75 | 12.58 | 13.23 | 13.39 | 13.45 | 13.89 | 13.10 | 13.11 | 13.15 |
| i-Butene (% by weight) | 18.35 | 17.72 | 17.59 | 18.19 | 18.14 | 18.12 | 18.89 | 17.36 | 17.45 | 17.52 |
| t-But-2-ene (% by weight) | 17.20 | 16.80 | 16.54 | 17.23 | 17.43 | 17.56 | 18.12 | 17.40 | 17.12 | 17.16 |
| i-But-2-ene (% by weight) | 13.55 | 13.27 | 13.06 | 13.58 | 13.80 | 13.86 | 14.29 | 13.48 | 13.50 | 13.55 |
| $C_{5+}$ (% by weight) | 5.43 | 4.16 | 4.34 | 4.09 | 4.34 | 4.70 | 4.61 | 3.77 | 3.81 | 3.71 |
| Conversion of n-butene (%) | 50.17 | 47.86 | 46.51 | 39.66 | 40.07 | 40.60 | 37.44 | 39.91 | 41.70 | 42.64 |
| Selectivity for iso-butene (%) | 64.11 | 69.57 | 67.61 | 69.92 | 69.11 | 67.05 | 68.67 | 71.10 | 70.85 | 70.83 |
| Selectivity for propene (%) | 15.67 | 13.06 | 14.56 | 13.33 | 13.32 | 14.46 | 13.49 | 12.46 | 12.69 | 13.15 |
| Selectivity for $C_{5+}$ (%) | 18.96 | 16.32 | 16.69 | 15.71 | 16.54 | 17.37 | 16.76 | 15.39 | 15.47 | 15.0 |
| Space/time yield for isobutene | 428.2 | 433.2 | 469.9 | 454.9 | 453.5 | 453.0 | 461.8 | 401.07 | 416.8 | 433.2 |

EXAMPLE 5

Pure n-pentene was passed over the catalyst prepared as described in Example 2, the reaction being carried out in a tubular reactor with an amount of catalyst of 20 cm³ under atmospheric pressure and at a temperature of 500° C.

The results of this experiment are summarized below:
WHSV for pentene: 2
WHSV for $H_2O$: 1
Conversion, % by weight: 25.3
Selectivity for i-pentene: 64.2%
Selectivity for $\leq C_5$: 17.3%
Selectivity for $C_{6+}$: 18.5%

To calculate these results, the following definitions were used;

Conversion % = 100 − Σ linear pentenes (reactor exit)

$$\text{Selectivity for } \leq C_5 = \frac{\% \text{ by weight of } \leq C_5 \cdot 100}{\Sigma \text{ n-pentenes}_{initial} - \Sigma \text{ n-pentenes}_{final}}$$

$$\text{Selectivity at } C_6 \frac{\% \text{ by weight of } C_{6+} \cdot 100}{\Sigma \text{ n-pentenes}_{initial} \Sigma - \text{ n-pentenes}_{final}}$$

$\leq C_5$: Hydrocarbons having less than 5 carbon atoms
$C_{6+}$: Hydrocarbons having 6 or more carbon atoms.

EXAMPLE 6

A catalyst prepared as described in Example 2 was calcined for 2 hours at 600° C. A $C_4$ starting mixture and steam were passed over the resulting product, as described in Example 1. This product showed no catalytic activity for the conversion of n-butene to iso-butene.

EXAMPLE 7 (for comparison)

50 g of the crystalline aluminosilicate prepared as described in Example 1 were suspended in a solution of 1 g of ammonium fluoride in 50 ml of water. After drying, and calzining for 3 hours at 450° C., the material contained 0.35% by weight of fluorine. A $C_4$ starting mixture and steam were passed over the resulting product, as described in Example 1. This product showed no catalytic activity for the conversion of n-butene to iso-butene.

EXAMPLE 8 (for comparison)

20 g of kaolin were suspended in 300 ml of aqueous 2N $MgCl_2$ solution for 3 hours at 100° C. The kaolin treated in this manner was filtered off, washed with water and dried. After calzination for 3 hours at 450° C. at $C_4$ starting mixture and steam were passed over the resulting product as described in Example 1. This product showed a catalytic activity for the conversion of n-butene to iso-butene only for three hours.

What is claimed is:

1. A process for the preparation of an isomerization catalyst which comprises co-molding a crystalline aluminosilicate having a molar ratio of silicon to aluminum of 100–10,000:1 with a kaolinite containing clay mineral and thereafter calcining the resultant molded product at 350°–550° C., said crystalline aluminosilicate containing 0.05 to 2% by-weight fluorine.

2. A process according to claim 1, wherein the resultant molded product additionally contains a binder or filler.

* * * * *